(12) United States Patent
Chang et al.

(10) Patent No.: US 11,058,400 B2
(45) Date of Patent: Jul. 13, 2021

(54) APPARATUS AND METHOD FOR EVALUATING PERFORMANCE OF ULTRASONIC TRANSDUCER

(71) Applicant: SOGANG UNIVERSITY RESEARCH FOUNDATION, Seoul (KR)

(72) Inventors: Jin Ho Chang, Seoul (KR); Jihun Jang, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 693 days.

(21) Appl. No.: 15/574,565

(22) PCT Filed: May 19, 2016

(86) PCT No.: PCT/KR2016/005313
§ 371 (c)(1),
(2) Date: Nov. 16, 2017

(87) PCT Pub. No.: WO2016/186464
PCT Pub. Date: Nov. 24, 2016

(65) Prior Publication Data
US 2018/0153517 A1    Jun. 7, 2018

(30) Foreign Application Priority Data
May 20, 2015 (KR) .................. 10-2015-0070412

(51) Int. Cl.
*A61B 8/00* (2006.01)
*A61B 8/08* (2006.01)
*A61N 7/00* (2006.01)
*H04R 29/00* (2006.01)
*A61B 17/00* (2006.01)
*A61B 18/00* (2006.01)

(52) U.S. Cl.
CPC .................. *A61B 8/52* (2013.01); *A61B 8/56* (2013.01); *A61B 8/58* (2013.01); *A61N 7/00* (2013.01);
(Continued)

(58) Field of Classification Search
CPC ........... A61B 2017/00707; A61B 2017/00725; A61B 2018/00898; A61B 2560/0223;
(Continued)

(56) References Cited

U.S. PATENT DOCUMENTS 5,517,994 A * 5/1996 Burke .................. B06B 1/0622
600/437
7,400,079 B2  7/2008 Omura et al.
(Continued)

FOREIGN PATENT DOCUMENTS

JP    2004-198442    7/2004
JP    2009-039246    2/2009
(Continued)

*Primary Examiner* — Christopher L Cook
(74) *Attorney, Agent, or Firm* — Duane Morris LLP; Gregory M. Lefkowitz

(57) ABSTRACT

An apparatus for evaluating performance of an ultrasonic transducer includes a transducer assembly having an ultrasonic transducer and an acoustic medium and configured to transmit and receive an ultrasonic wave, a storage unit configured to store a reference signal value which represents the performance of the ultrasonic transducer, and a processing unit configured to control the transducer assembly to emit ultrasonic wave and receive a response (echo) signal thereto to measure a magnitude or energy amount of the response signal, the processing unit comparing a measured value with the reference signal value stored in the storage unit to evaluate the performance of the ultrasonic transducer.

19 Claims, 9 Drawing Sheets

(52) U.S. Cl.
CPC .... *H04R 29/00* (2013.01); *A61B 2017/00707* (2013.01); *A61B 2017/00725* (2013.01); *A61B 2018/00898* (2013.01); *A61B 2560/0223* (2013.01); *A61B 2560/0228* (2013.01); *A61B 2560/0238* (2013.01); *A61N 2007/0078* (2013.01)

(58) Field of Classification Search
CPC .... A61B 2560/0228; A61B 2560/0238; A61B 8/52; A61B 8/56; A61B 8/58; A61N 2007/0078; A61N 7/00
See application file for complete search history.

(56) References Cited

U.S. PATENT DOCUMENTS

| | | |
|---|---|---|
| 10,028,729 B2 * | 7/2018 | Beaty ................. A61B 8/58 |
| 2002/0049381 A1 | 4/2002 | Eck et al. |
| 2007/0220980 A1 * | 9/2007 | Tanaka ............. G01S 15/8918 73/649 |
| 2009/0093719 A1 * | 4/2009 | Pelissier ............. A61B 8/467 600/447 |
| 2012/0313486 A1 | 12/2012 | Jung et al. |
| 2013/0283916 A1 | 10/2013 | Hersey |
| 2014/0241115 A1 * | 8/2014 | Thattari Kandiyil ................ G01S 7/52004 367/13 |

FOREIGN PATENT DOCUMENTS

| | | |
|---|---|---|
| KR | 10-2008-0039634 | 5/2008 |
| KR | 10-2009-0052592 | 5/2009 |
| KR | 10-2012-0101640 | 9/2012 |

\* cited by examiner

[FIG. 1]
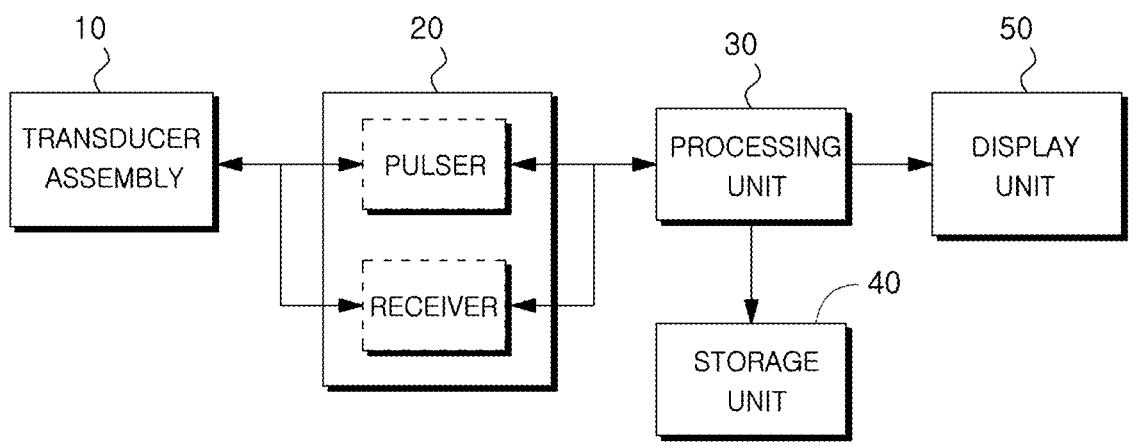

[FIG. 2]
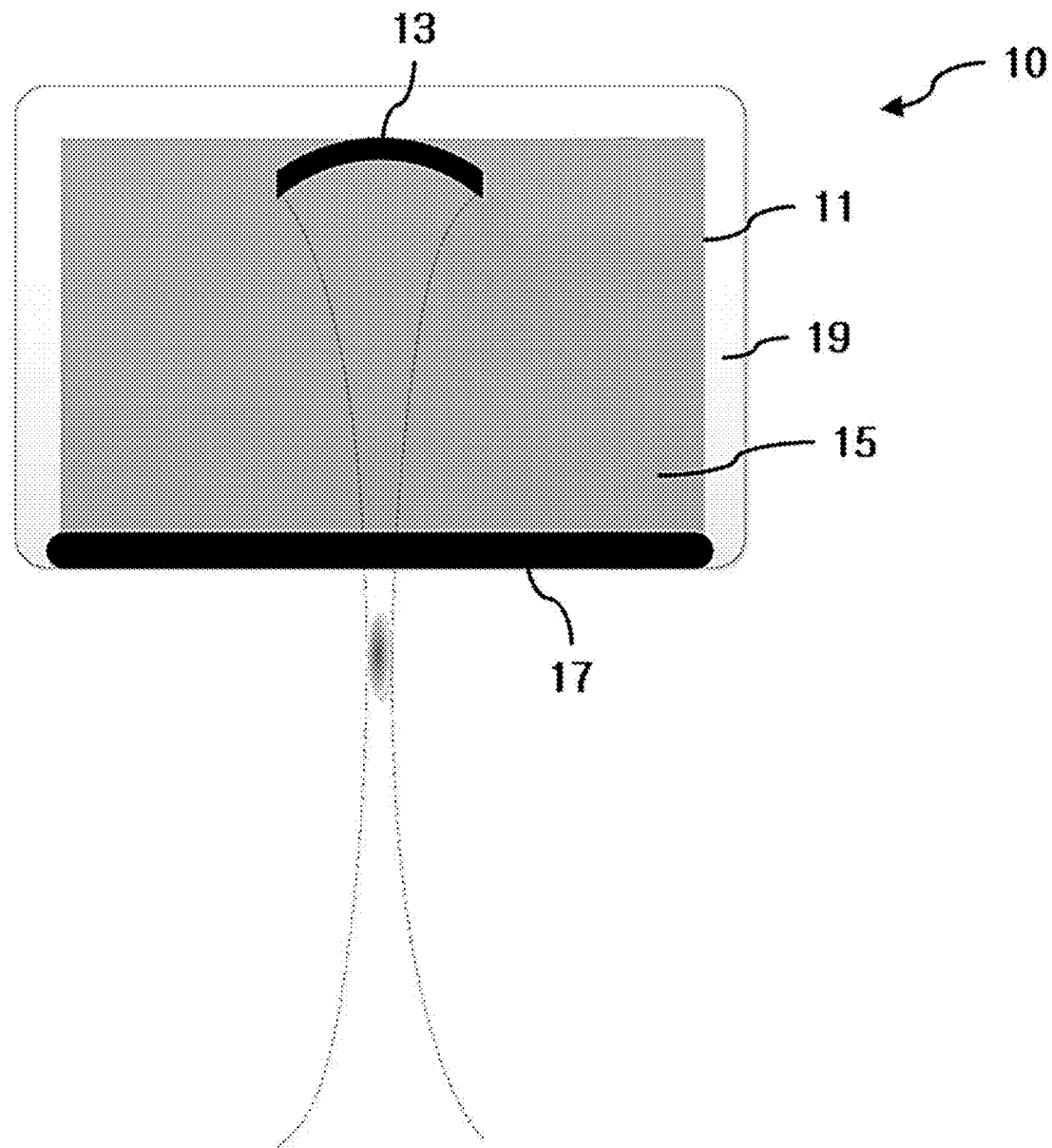

[FIG. 3]
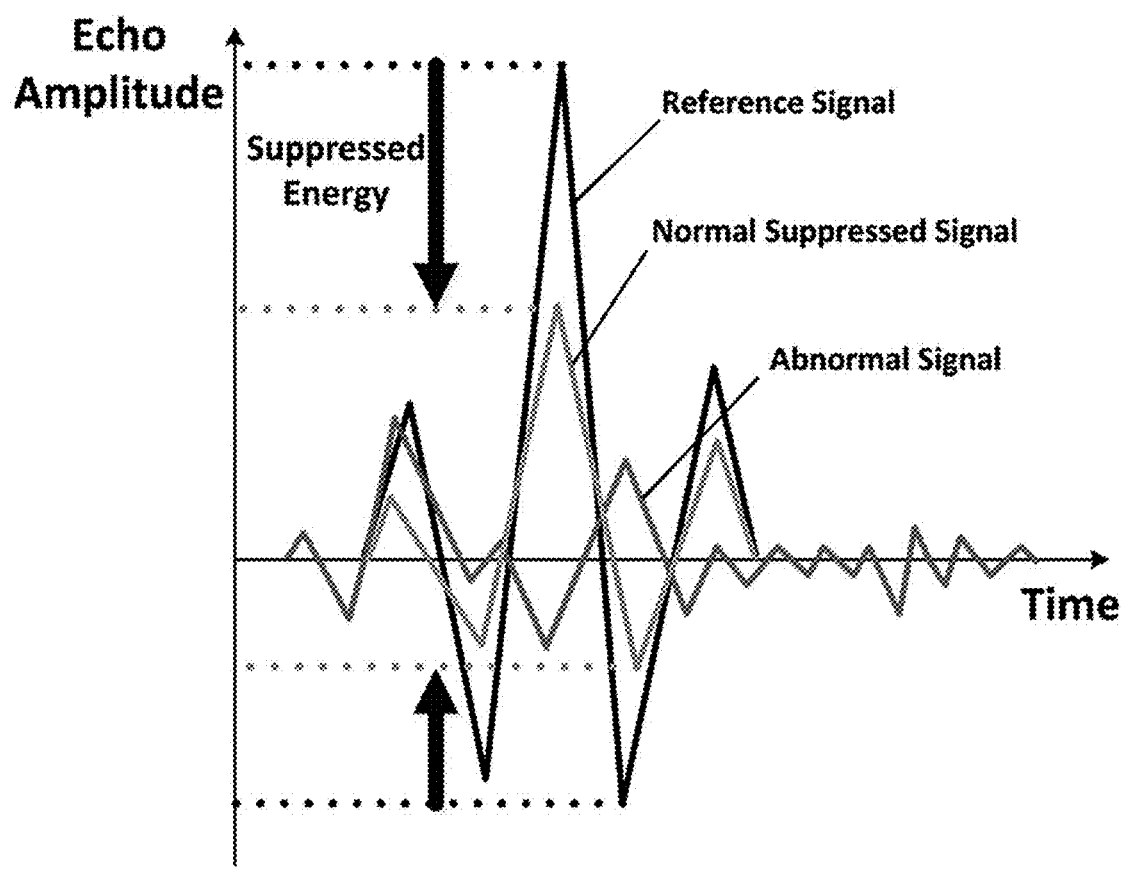

[FIG. 4a]
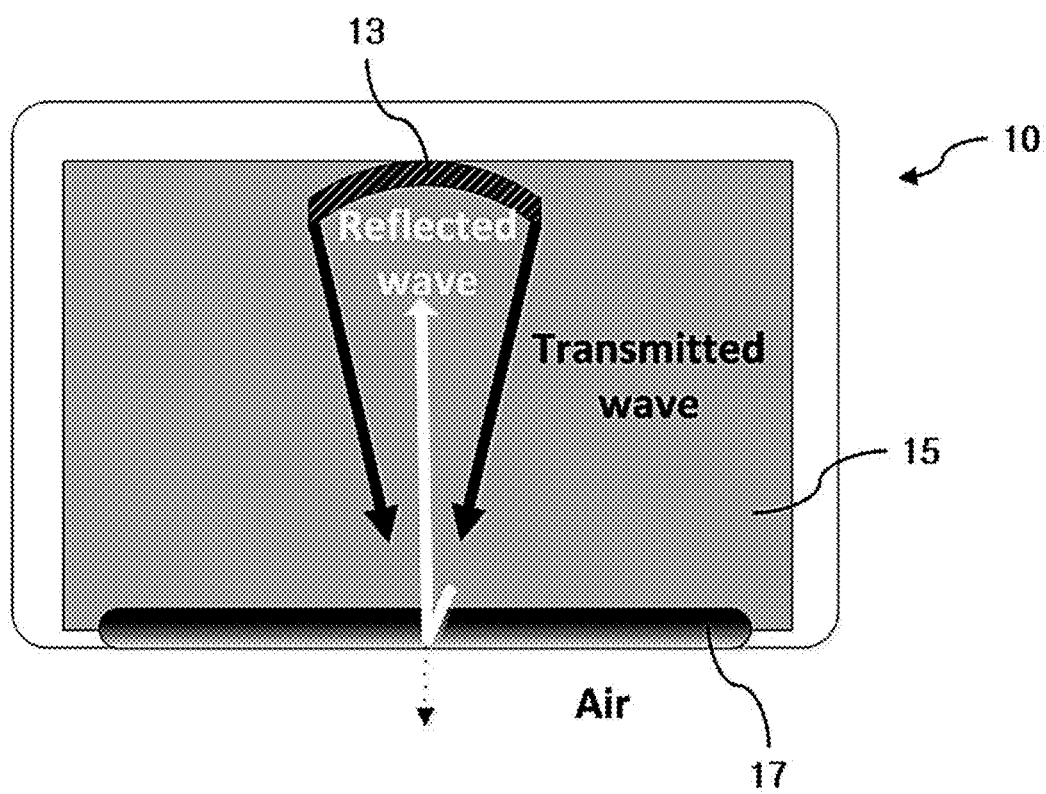

[FIG. 4b]
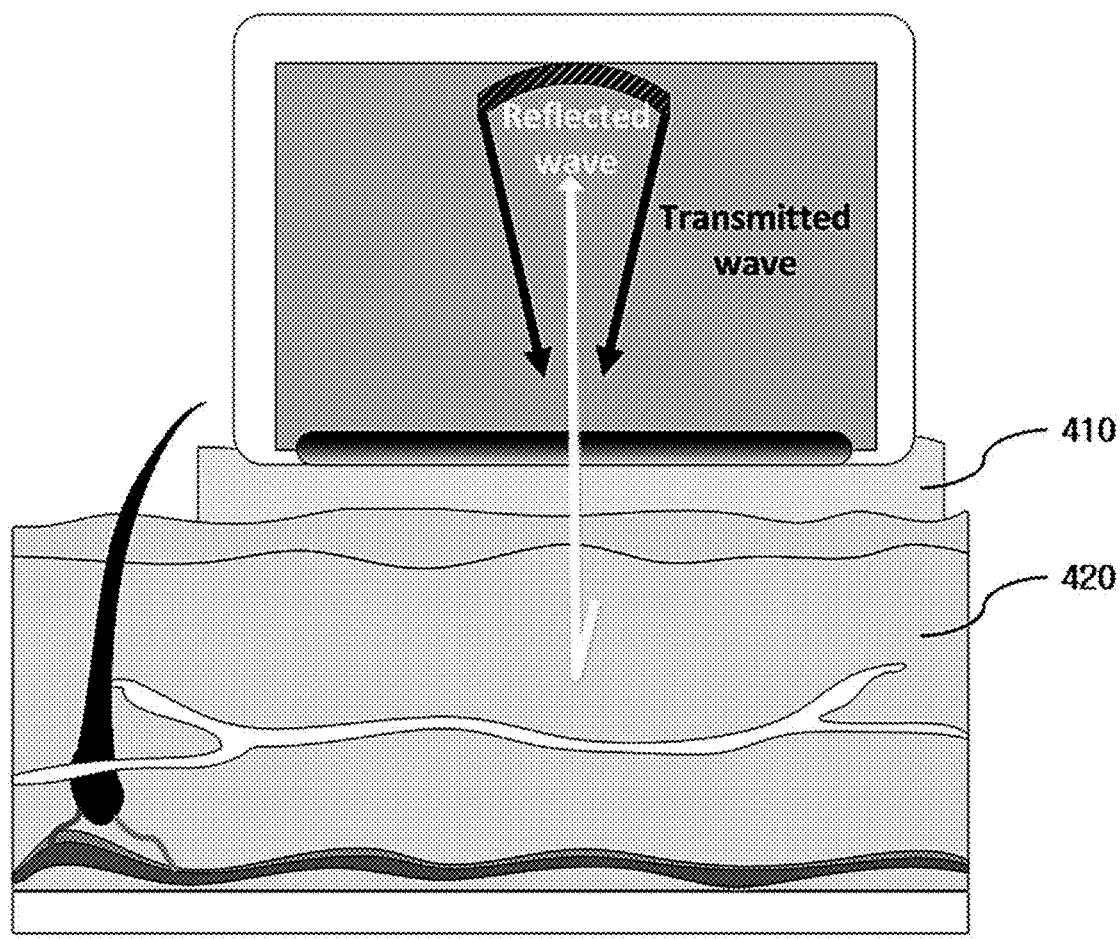

[FIG. 4c]
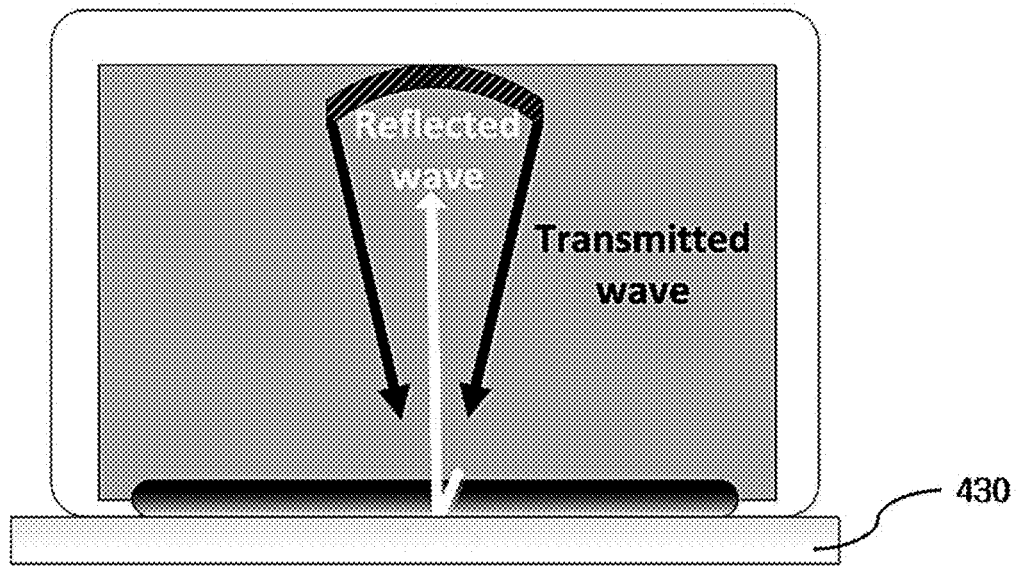
[FIG. 4d]
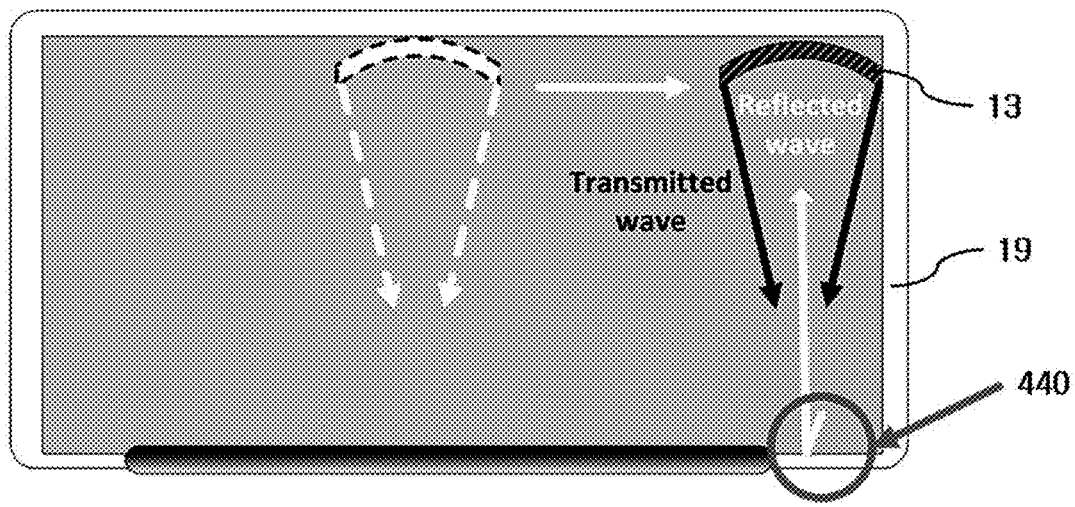

[FIG. 5]
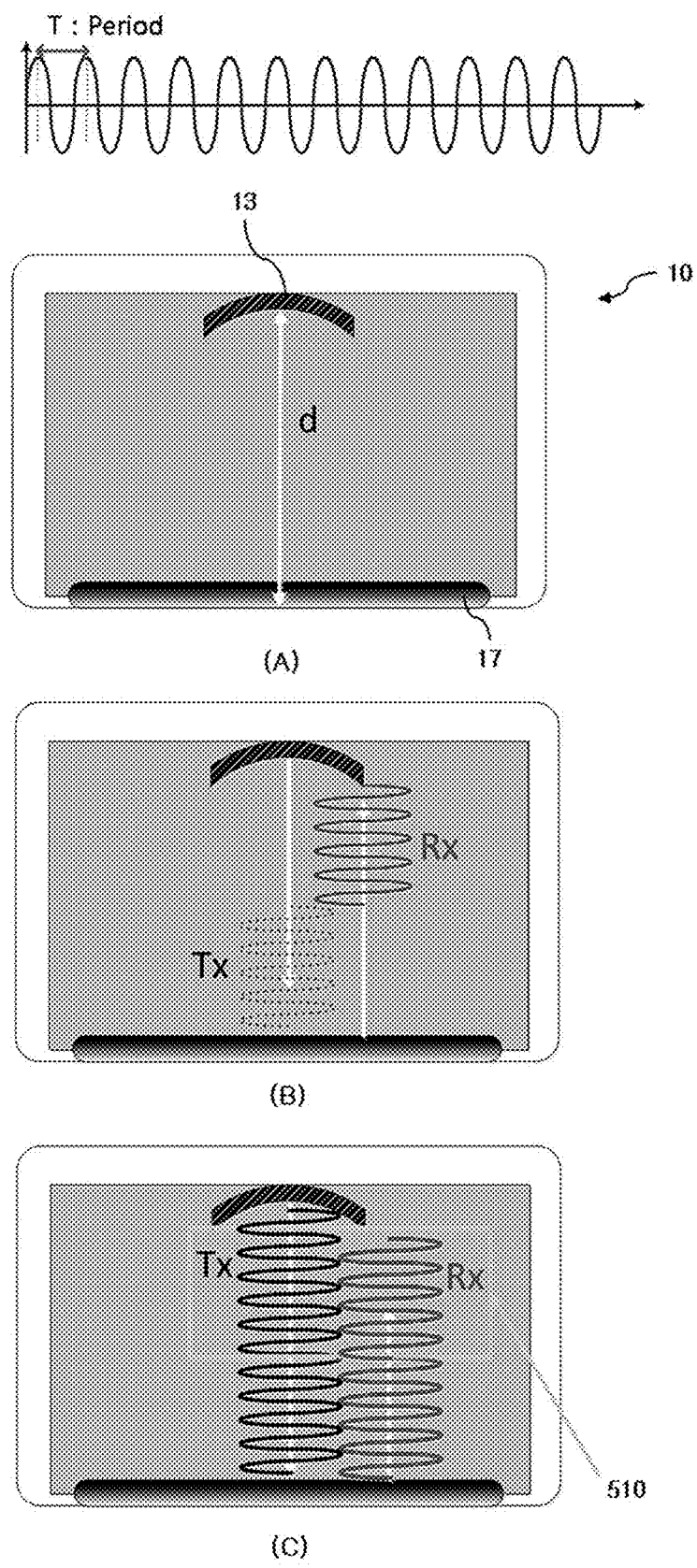

[FIG. 6]
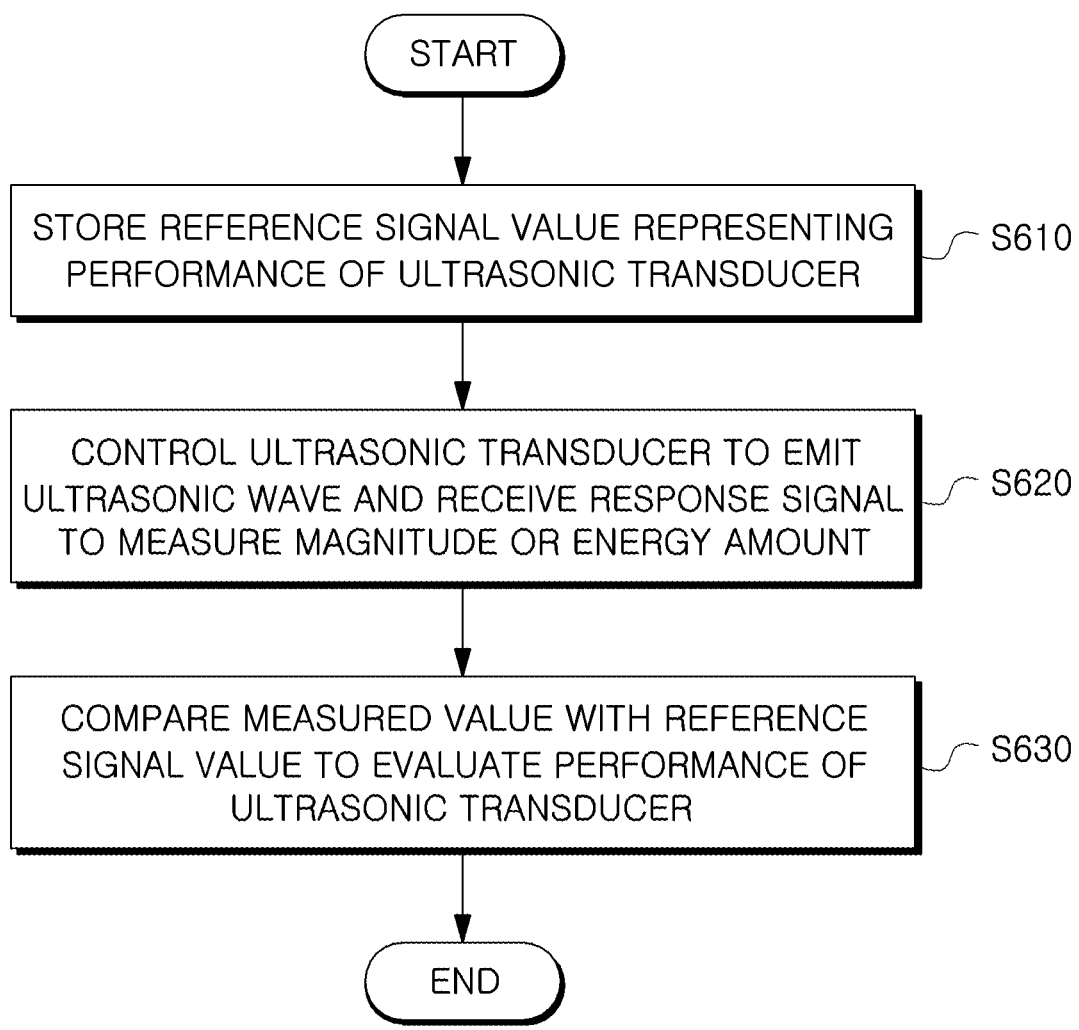

[FIG. 7]
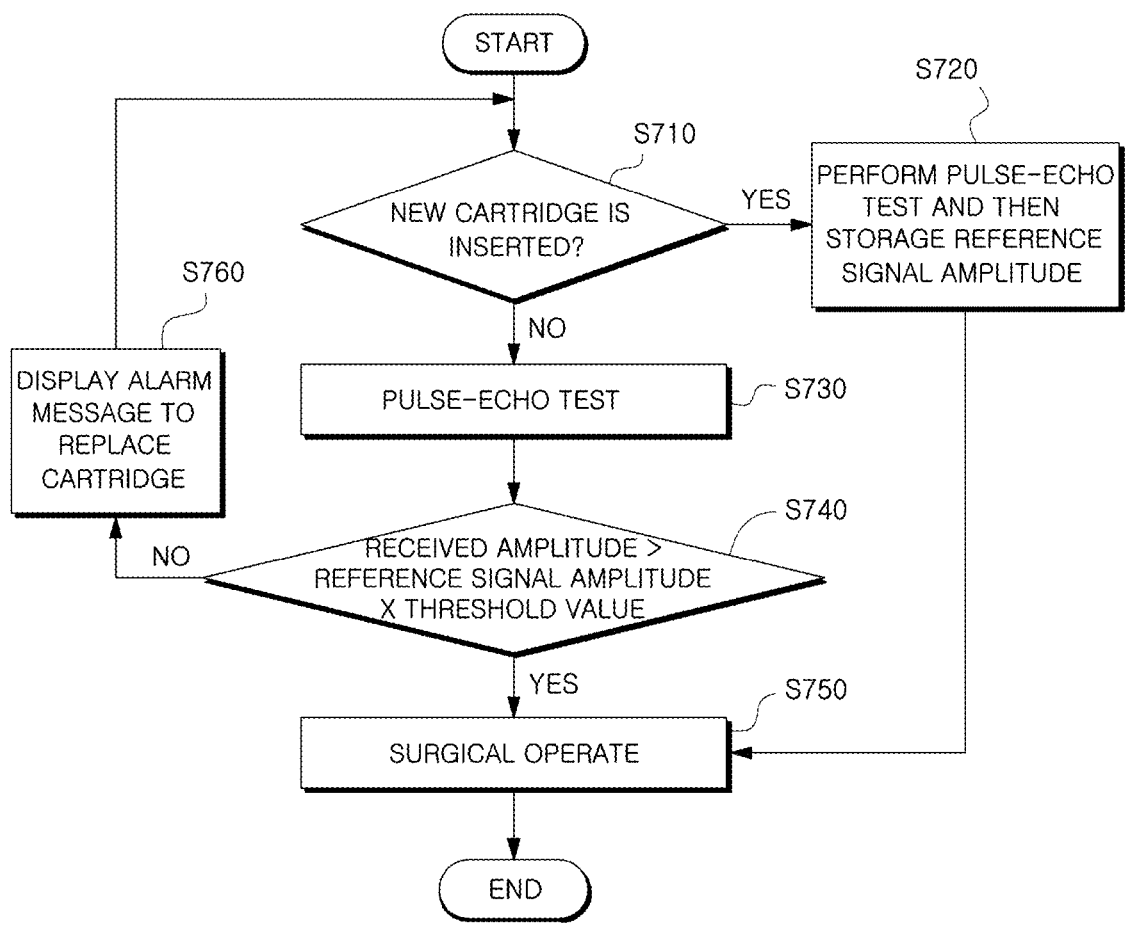

APPARATUS AND METHOD FOR EVALUATING PERFORMANCE OF ULTRASONIC TRANSDUCER

CROSS-REFERENCE TO RELATED APPLICATIONS

This application is a § 371 national stage entry of International Application No. PCT/KR2016/005313, filed on May 19, 2016, which claims priority to South Korean Patent Application No. 10-2015-0070412, filed on May 20, 2015, the entire contents of which are incorporated herein by reference.

TECHNICAL FIELD

This disclosure relates to relates to an ultrasonic transducer for generating ultrasonic waves and receiving a response signal, in particular, to an apparatus and method for evaluating performance of a therapeutic ultrasonic transducer to check how much the performance of the therapeutic ultrasonic transducer is degraded in comparison to an initial state, and a recording medium in which the method is recorded.

BACKGROUND ART

Ultrasonic waves are used in a medical field such as an image diagnosis device, an ultrasonic wave treatment device, an ultrasonic wave cleaning device or various equipment diagnosis devices, and accordingly, there is demanded a technique for measuring and controlling an output level of the ultrasonic transducer.

In the past, in order to measure an acoustic output of an ultrasonic transducer, a radiation force balance method, a planar scanning method, a calorimeter method or the like has been used.

The radiation force balance method is a method of measuring an acoustic output in a simple way by simply applying ultrasonic wave energy to a sound absorbing material. Since the radiation force balance method may measure only an average acoustic pressure of the sound absorbing material without finding a sound intensity at a treatment site or a specific point, it is difficult to judge a therapeutic effect of a local site. In particular, a measurement target used for the measurement melted when exposed to an ultrasonic wave having a power of about 20 W or more, and thus the radiation force balance method may not be used for measuring a power of an ultrasonic wave having a power of about 20 W or more.

The planar scanning method is a method of scanning a distribution area of ultrasonic waves by using a hydrophone. In the planar scanning method, a transducer is vertically and horizontally aligned using at least five axes based on motor control, and an acoustic pressure or intensity at all media in which ultrasonic wave energy is transmitted may be accurately measured. Thus, the planar scanning method is useful to quantitatively analyze an acoustic pressure of a therapeutic transducer, but it requires a long time for the measurement since a large area should be scanned to measure an output of the ultrasonic wave.

The calorimeter method is a method of measuring a rising temperature of water caused by ultrasonic waves. Since the spatial distribution of acoustic pressure in water is not uniform, it is necessary to measure temperature at several places by using a number of thermometers. Thus, the measuring process is complicated and a long time is needed to install the thermometers.

Meanwhile, in the therapeutic ultrasonic wave treatment, a high voltage should be applied and a therapeutic transducer should be vibrated for a long time, which may generate a deterioration effect. Also, unlike a general ultrasonic wave image transducer, the therapeutic transducer may be used during a very short period. This deterioration effect is the biggest factor that deteriorates the effect of the therapeutic ultrasonic wave treatment, and it is very important to determine the replacement time of the ultrasonic transducer in a timely manner to ensure the therapeutic effect. However, it is not easy for an operator, for example a physician, to evaluate an acoustic output of the transducer by using an acoustic measuring device such as a hydrophone, and the price is very expensive and unrealistic.

Therefore, instead of measuring an acoustic output of the ultrasonic transducer described above, it is necessary to propose a technical means for evaluating the performance degradation of the transducer and selecting the replacement time in a simple way while utilizing the basic structure of the therapeutic ultrasonic transducer. The following document introduces various techniques for measuring an acoustic output of an ultrasonic transducer, but these techniques are still unsuitable for applying to a real medical environment.

RELATED LITERATURES

Korean Unexamined Patent Publication No. 10-2009-0052592, Apparatus and method for measuring ultrasonic power by using latent heat, Korea Research Institute of Standards and Science, published on May 26, 2009

DISCLOSURE

Technical Problem

The present disclosure is directed to solving the problem that in an actual medical environment, not a highly equipped laboratory, there is no way for an operator to simply check the output degradation of a therapeutic ultrasonic transducer, and thus overcoming the limitations that it is impossible to propose the performance and suitable replacement time of the ultrasonic transducer since the replacement time of the ultrasonic transducer is determined only by the number of output-guaranteed transducer treatments marked by an ultrasonic transducer manufacturer regardless of an actual output of the ultrasonic transducer.

Technical Solution

In one general aspect, there is provided an apparatus for evaluating performance of an ultrasonic transducer, comprising: a transducer assembly having an ultrasonic transducer and an acoustic medium and configured to transmit and receive an ultrasonic wave; a storage unit configured to store a reference signal value which represents the performance of the ultrasonic transducer; and a processing unit configured to control the transducer assembly to emit ultrasonic wave and receive a response (echo) signal thereto to measure a magnitude or energy amount of the response signal, the processing unit comparing a measured value with the reference signal value stored in the storage unit to evaluate the performance of the ultrasonic transducer.

In the apparatus for evaluating performance of an ultrasonic transducer according to an embodiment, the response signal may be generated when the ultrasonic wave emitted from the ultrasonic transducer is reflected or totally reflected according to a physical characteristic of the transducer assembly.

In the apparatus for evaluating performance of an ultrasonic transducer according to an embodiment, when no object comes into contact with an outer surface of the transducer assembly, the ultrasonic wave emitted from the ultrasonic transducer may be totally reflected at the inside of the transducer assembly due to a difference in acoustic impedance between the acoustic medium of the transducer assembly and the outer surface of the transducer assembly, and the ultrasonic transducer may receive the totally reflected response signal to measure the magnitude or energy amount.

In the apparatus for evaluating performance of an ultrasonic transducer according to an embodiment, when a measurement target comes into contact with an outer surface of the transducer assembly, the ultrasonic wave emitted from the ultrasonic transducer may be reflected by the measurement target through the acoustic medium, and the ultrasonic transducer may receive the reflected response signal to measure the magnitude or energy amount.

In the apparatus for evaluating performance of an ultrasonic transducer according to an embodiment, when a steel reflector comes into contact with an outer surface of the transducer assembly, the ultrasonic wave emitted from the ultrasonic transducer may be reflected by the steel reflector through the acoustic medium, and the ultrasonic transducer may receive the reflected response signal to measure the magnitude or energy amount.

In the apparatus for evaluating performance of an ultrasonic transducer according to an embodiment, when the ultrasonic transducer is relocated to face a reflecting structure in the transducer assembly, the ultrasonic wave emitted from the ultrasonic transducer may be reflected by the reflecting structure through the acoustic medium, and the ultrasonic transducer may receive the reflected response signal to measure the magnitude or energy amount.

In the apparatus for evaluating performance of an ultrasonic transducer according to an embodiment, the processing unit may generate an alarm to notify that the performance of the ultrasonic transducer is degraded, when the difference between the reference signal value and the measured value is over a preset critical range. In addition, the critical range may be set using a property that the degree of degradation of the ultrasonic transducer is proportional to the degree of magnitude reduction of the response signal. Further, the transducer assembly may be formed using an exchangeable cartridge and be controlled by the processing unit in a state of being inserted into a handpiece for ultrasonic treatment, and the alarm may be a message which demands an exchange of the cartridge.

In the apparatus for evaluating performance of an ultrasonic transducer according to an embodiment, the transducer assembly may include: a body configured to support the transducer assembly; an ultrasonic transducer accommodated in the body and configured to generate an ultrasonic wave; an acoustic impedance boundary area spaced apart from the ultrasonic transducer by a predetermined distance and formed at an end of the body in a direction in which the ultrasonic wave is emitted; and an acoustic medium filled in the body to transmit the ultrasonic wave. In addition, the distance between the ultrasonic transducer and the boundary area may be proportional to the number of cycles of the ultrasonic signal emitted from the ultrasonic transducer and in reversely proportional to a frequency of the ultrasonic signal. Further, the processing unit may set the number of cycles of the ultrasonic signal emitted from the ultrasonic transducer to be a half or less of a value obtained by multiplying the distance between the ultrasonic transducer and the boundary area by a frequency of the ultrasonic signal and dividing by a speed of the ultrasonic signal, thereby preventing an interference between the signal emitted from the ultrasonic transducer and the signal received thereto.

In another aspect of the present disclosure, there is also provided a method for evaluating performance of an ultrasonic transducer, which evaluates the performance of a transducer assembly having an ultrasonic transducer and an acoustic medium to transmit and receive an ultrasonic wave, the method comprising: storing a reference signal value which represents the performance of the ultrasonic transducer by using a memory; controlling the transducer assembly to emit an ultrasonic wave and receiving a response (echo) signal thereto, and measuring a magnitude or energy amount of the response signal; and comparing a measured value with the reference signal value stored in the memory by using at least one processor to evaluate the performance of the ultrasonic transducer.

In the method for evaluating performance of an ultrasonic transducer according to an embodiment, the response signal may be generated when the ultrasonic wave emitted from the ultrasonic transducer is reflected or totally reflected according to a physical characteristic of the transducer assembly.

In the method for evaluating performance of an ultrasonic transducer according to an embodiment, the step of measuring a magnitude or energy amount of the response signal may include: controlling the transducer assembly to emit an ultrasonic wave in a state where no object comes into contact with an outer surface of the transducer assembly; receiving a totally reflected response signal by using the ultrasonic transducer as the ultrasonic wave emitted from the ultrasonic transducer is totally reflected at the inside of the transducer assembly due to a difference in acoustic impedance between the acoustic medium of the transducer assembly and the outer surface of the transducer assembly; and measuring a magnitude or energy amount of the received response signal.

In the method for evaluating performance of an ultrasonic transducer according to an embodiment, the step of measuring a magnitude or energy amount of the response signal may include: controlling the transducer assembly to emit an ultrasonic wave in a state where a measurement target comes into contact with an outer surface of the transducer assembly; receiving a reflected response signal by using the ultrasonic transducer as the ultrasonic wave emitted from the ultrasonic transducer is reflected by the measurement target through the acoustic medium; and measuring a magnitude or energy amount of the received response signal.

In the method for evaluating performance of an ultrasonic transducer according to an embodiment, the step of measuring a magnitude or energy amount of the response signal may include: controlling the transducer assembly to emit an ultrasonic wave in a state where a steel reflector comes into contact with an outer surface of the transducer assembly; receiving a reflected response signal by using the ultrasonic transducer as the ultrasonic wave emitted from the ultrasonic transducer is reflected by the steel reflector through the acoustic medium; and measuring a magnitude or energy amount of the received response signal.

In the method for evaluating performance of an ultrasonic transducer according to an embodiment, the step of measuring a magnitude or energy amount of the response signal may include: relocating the ultrasonic transducer to face a reflecting structure in the transducer assembly by using a driving unit; controlling the transducer assembly to emit an ultrasonic wave; receiving a reflected response signal by using the ultrasonic transducer as the ultrasonic wave emitted from the ultrasonic transducer is reflected by the reflecting structure through the acoustic medium; and measuring a magnitude or energy amount of the received response signal.

The method for evaluating performance of an ultrasonic transducer according to an embodiment may further comprise: generating an alarm to notify that the performance of the ultrasonic transducer is degraded, when the difference between the reference signal value and the measured value is over a preset critical range. In addition, the critical range may be set using a property that the degree of degradation of the ultrasonic transducer is proportional to the degree of magnitude reduction of the response signal. Further, the transducer assembly may include a body configured to support the transducer assembly, an ultrasonic transducer accommodated in the body and configured to generate an ultrasonic wave, a boundary area spaced apart from the ultrasonic transducer by a predetermined distance and formed at an end of the body in a direction in which the ultrasonic wave is emitted, and an acoustic medium filled in the body to transmit the ultrasonic wave, and the number of cycles of the ultrasonic signal emitted from the ultrasonic transducer may be set to be a half or less of a value obtained by multiplying the distance between the ultrasonic transducer and the boundary area by a frequency of the ultrasonic signal and dividing by a speed of the ultrasonic signal, thereby preventing an interference between the signal emitted from the ultrasonic transducer and the signal received thereto.

Meanwhile, in another aspect of the present disclosure, there is also provided a computer-readable recording medium in which a program for executing the method for evaluating performance of an ultrasonic transducer in a computer is recorded.

Advantageous Effects

According to embodiments of the present disclosure, by using the feature that a reflection signal is generated when an ultrasonic wave passes through medium having different acoustic impedances, an acoustic measurement device such as an expensive hydrophone is not necessary, and an operator may easily evaluate the deterioration effect automatically or manually, which is effective in determining the replacement time of the therapeutic ultrasonic transducer. Thus, it may be possible to reduce costs by preventing unnecessary cartridge replacement while maintaining the therapeutic performance of the ultrasonic treatment equipment.

DESCRIPTION OF DRAWINGS

FIG. 1 is a block diagram showing an apparatus for measuring performance of an ultrasonic transducer according to an embodiment of the present disclosure.

FIG. 2 is a diagram showing a transducer assembly adopted in an ultrasonic system according to embodiments of the present disclosure.

FIG. 3 is a diagram for illustrating a technical principle for evaluating performance of an ultrasonic transducer at the ultrasonic system according to embodiments of the present disclosure.

FIGS. 4a to 4d are diagrams showing various embodiments of a method for evaluating performance of an ultrasonic transducer according to embodiments of the present disclosure.

FIG. 5 is a diagram for illustrating a method for determining a distance between the ultrasonic transducer and a boundary area (film) at the transducer assembly adopted in the ultrasonic system according to embodiments of the present disclosure.

FIG. 6 is a flowchart for illustrating a method for evaluating performance of an ultrasonic transducer according to an embodiment of the present disclosure.

FIG. 7 is a flowchart for illustrating a method for utilizing the method for evaluating performance of an ultrasonic transducer according to embodiments of the present disclosure to the ultrasonic system.

<Reference Signs>

10: transducer assembly
20: ultrasonic wave transmitting/receiving unit
30: processing unit
40: storage unit
50: display unit
11: body                13: ultrasonic transducer
15: acoustic medium     17: boundary area or film
19: handpiece/housing case

BEST MODE

An apparatus for evaluating performance of an ultrasonic transducer according to an embodiment of the present disclosure includes a transducer assembly having an ultrasonic transducer and an acoustic medium and configured to transmit and receive an ultrasonic wave, a storage unit configured to store a reference signal value which represents the performance of the ultrasonic transducer, and a processing unit configured to control the transducer assembly to emit ultrasonic wave and receive a response (echo) signal thereto to measure a magnitude or energy amount of the response signal, the processing unit comparing a measured value with the reference signal value stored in the storage unit to evaluate the performance of the ultrasonic transducer.

Mode for Invention

Prior to describing the present disclosure, the characteristics of the ultrasonic transducer and the problems caused by the use environment of the therapeutic ultrasonic transducer will be introduced briefly, and the technical means adopted in the embodiments of the present disclosure to solve this problem will be proposed in sequence.

In general, an ultrasonic transducer is a consumable product and exhibits the degradation effect of a piezoelectric element due to continuous use. The degradation effect is one of the main factors that degrade the performance of the piezoelectric element. The ultrasonic transducer may generate spatial resolution based on its structural and physical characteristics. In particular, in case of therapeutic ultrasonic transducer, a high input voltage is applied for long time to generate high output, and thus the degradation effect tends to occur quickly in comparison to an ultrasonic transducer for image. Thus, the acoustic output of the therapeutic ultrasonic transducer is lowered, and if the acoustic output is relatively very low compared to a transducer in a normal state, the therapeutic effect for the lesion is reduced.

However, in the present medical environment, not in a highly-equipped laboratory, there is no suggestion for an operator to simply check the output degradation of a therapeutic ultrasonic transducer, and thus the operator relies on the number of output-guaranteed transducer treatments marked by an ultrasonic transducer manufacturer or seller, regardless of the actual output of the ultrasonic transducer. For example, the number of output-guaranteed transducer treatments is marked on a product, or the replacement of the ultrasonic transducer is notified after a fixed preset number of treatments through an ultrasonic system.

In this replacement scheme, the performance of the ultrasonic transducer may have adequately degraded, but in some cases the replacement time has already passed, or the ultrasonic transducer may be replaced even though it is still sufficiently usable since the degradation effect is not serious. In other words, this replacement scheme not only causes complaints of patients who have been treated with a transducer that has no therapeutic effect but also damages the hospital's image and continuously cause damages due to re-operation. Therefore, there is a need to develop a method for allowing operators to easily check ultrasonic wave output degradation at an operation site.

In the embodiments of the present disclosure proposed below, a technical means for checking the output degradation of a transducer in a simple way by utilizing the shape and structure of an existing therapeutic ultrasonic transducer and the characteristics of ultrasonic waves will be proposed to solve the above problems. In particular, the ultrasonic wave has a characteristic in that it is reflected when passing through a medium having different acoustic impedances. Thus, the embodiments of the present disclosure utilize a method of generating an ultrasonic wave in a state where a separate acoustic medium does not come into contact with a surface of the therapeutic ultrasonic transducer, obtaining a signal reflected or totally reflected on the surface to the ultrasonic transducer, and then analyzing a magnitude of the signal in order to determine the degradation of performance of the ultrasonic transducer.

Hereinafter, the embodiments of the present disclosure will be described in detail with reference to the drawings.

FIG. 1 is a block diagram showing an apparatus for measuring performance of an ultrasonic transducer according to an embodiment of the present disclosure, and the apparatus includes a transducer assembly 10, a processing unit 30 and storage unit 40, and includes optionally a display unit 50. The apparatus may further include an ultrasonic wave transmitting/receiving unit 20 for generating an ultrasonic signal and receiving a reflected (echo) signal thereof.

The transducer assembly 10 includes an ultrasonic transducer and an acoustic medium to transmit and receive an ultrasonic wave. The ultrasonic wave transmitting/receiving unit 20 receives a command from the processing unit 30 to generate an ultrasonic signal by controlling a pulser, applies the ultrasonic signal to an ultrasonic transducer provided at the transducer assembly 10, and receives a response signal received from the surface of the ultrasonic transducer provided at the transducer assembly 10 by means of the receiving unit. At this time, the response signal is generated as the ultrasonic wave emitted through the ultrasonic transducer is reflected or totally reflected due to the physical characteristic of the transducer assembly.

In particular, in the embodiment of the present disclosure, the technical means is explained based on the case where a response signal is generated by means of the total reflection in the transducer assembly 10 in a state where the transducer assembly 10 is in contact with the outside air, namely in an initial state without any contact, but it is also possible to use various phantoms having high reflection characteristics in place of the air to be contacted. More detailed applications will be described later with reference to FIGS. 4a to 4d.

The storage unit 40 stores a reference signal value which represents the performance of the ultrasonic transducer. The reference signal value may be a value measured in advance by an ultrasonic transducer manufacturer at factory shipments, or a value measured at initial installation may also be used a reference signal value depending on the use environments.

The processing unit 30 controls the transducer assembly 10 to emit an ultrasonic wave and receives a response (echo) signal thereto to measure a magnitude or energy amount of the response signal, and compares a measured value with the reference signal value stored in the storage unit 40 to evaluate the performance of the ultrasonic transducer. For this, the processing unit 30 may store the received response signal in a temporary storage space such as a register or memory, and then compare the stored response signal with a previously stored reference signal value by means of a comparator.

In addition, the processing unit 30 may generate an alarm message notifying that the performance of the ultrasonic transducer is degraded, when the difference between the reference signal value stored in the storage unit 40 and the value measured by the transducer assembly 10 is over a predetermined critical range. In this case, the critical range may be set using a property that the degree of degradation of the ultrasonic transducer is proportional to the degree of magnitude reduction of the response signal.

The display unit 50 allows the ultrasonic system according to this embodiment to interact with a user. When the processing unit 30 determines that the present degree of degradation of the ultrasonic transducer exceeds the preset critical range, the display unit may display an alarm message to notify that the transducer assembly 10 should be replaced.

FIG. 2 is a diagram showing the transducer assembly 10 adopted at the ultrasonic system according to embodiments of the present disclosure, and the transducer assembly 10 includes a body 11 supporting the transducer assembly, an ultrasonic transducer 13 accommodated in the body 11 to generate an ultrasonic wave, an acoustic medium 15 filled in the body 11 to transmit the ultrasonic wave, and an acoustic impedance boundary area 17 spaced apart from of the ultrasonic transducer 13 by a predetermined distance and formed at one end of the body 11 in a direction in which the ultrasonic wave is emitted (if the acoustic medium is water, the boundary area may be a film, and if a film is mentioned as the boundary area, it is assumed that the acoustic medium is water). The transducer assembly 10 may be entirely fabricated in the form of an exchangeable cartridge and controlled by the processing unit in a state of being inserted into a handpiece 19 for ultrasonic treatment. In this case, as described above, an alarm notifying that the degree of degradation exceeds an appropriate critical range may be expressed as a message demanding replacement of the cartridge.

The therapeutic ultrasonic transducer may be a cartridge type as shown in FIG. 2, and there is a boundary area or film 17 through which ultrasonic wave energy transmits. Due to the nature of the ultrasonic wave, an acoustic medium such as water is demanded to propagate energy, and in order to preserve the acoustic medium, the surface of the cartridge may be made of a waterproof material such as the film 17.

In addition, the ultrasonic wave has a characteristic in that it is reflected when passing through a medium having different acoustic impedances. Therefore, if an ultrasonic wave is generated in a state where the transducer assembly 10 is left in the air without making a treatment spot, namely another acoustic medium (which means an external acoustic medium other than the acoustic medium 15 inside the transducer assembly), to contact the surface of the cartridge, the ultrasonic wave is almost totally reflected at the end of the filled acoustic medium, namely at the film 17. Since the air has very low acoustic impedance, unlike the acoustic medium such as water, it is difficult for the ultrasonic wave to pass from water into the air. Thus, as shown in FIG. 2, the ultrasonic signal emitted from the ultrasonic transducer 13 of the transducer assembly 10 may be focused at the outside after passing through the film 17, or may be reflected or totally reflected at the inside of the transducer assembly 10 as described above.

FIG. 3 is a diagram for illustrating a technical principle for evaluating the performance of the ultrasonic transducer in the ultrasonic system according to embodiments of the present disclosure, and each signal depicted in the graph has the following meaning.

Reference Signal: a magnitude of a reference signal stored in the memory or a signal of a newly produced transducer at an initial production stage.

Normal Suppressed Signal: a magnitude of a response signal whose magnitude is reduced due to the degradation effect of the transducer.

Abnormal Signal: a signal when a skin or another medium comes into contact with a front surface of the transducer assembly or the cartridge. The abnormal signal has a longer duration time in comparison to a normal signal and exhibits signal distribution with no tendency. If the abnormal signal appears, an alarm message for demanding re-measurement may be displayed to the operator through the display unit.

As described above, when a degradation effect occurs at the ultrasonic transducer, the overall transmission and reception characteristics of the piezoelectric element are degraded, and thus a smaller reflected signal is measured in comparison to the normal ultrasonic transducer. Therefore, a magnitude of a reflected signal of the transducer in an initial normal state is measured, and then, before an operator uses an instrument, for example when booting a surgical instrument or just before replacing the therapeutic ultrasonic transducer or performing a surgical operation, the ultrasonic reflected signal is automatically or manually acquired, and if the difference in magnitude lowers below a certain level, the therapeutic ultrasonic transducer is replaced, which may give a stable and appropriate replacement time and prevent unnecessary cartridge replacement. Also, by replacing the transducer in a timely manner, it is possible to minimize the reduction of treatment efficiency caused by performance degradation.

As proposed in FIG. 2, the transducer assembly adopted by the present disclosure has an acoustic medium for propagating the ultrasonic wave generated from the ultrasonic transducer, so that the ultrasonic wave may be transmitted at least to the film even though another acoustic medium is not brought into contact with the surface of the ultrasonic transducer. However, due to the characteristics of the ultrasonic wave, energy is not able to be transferred to the outside (air) of the transducer assembly, which has a great difference in acoustic impedance compared with the acoustic medium filled in the transducer assembly, so that the energy is substantially totally reflected and returns to the transducer. Therefore, it is possible to evaluate the performance degradation of the transducer due to degradation effects by measuring the magnitude or energy amount of the returning signal. This technique utilizes the phenomenon that when the degradation effect occurs, the transmission and reception characteristics of the piezoelectric element are all lowered. As shown in the graph of FIG. 3, it is possible to determine the replacement time of the cartridge by checking that the magnitude of the energy is lowered, and it is effective in reducing the cost caused by the replacement of the cartridge by preventing the unnecessary replacement.

FIGS. 4a to 4d are diagrams for illustrating various embodiments of a method for evaluating performance of an ultrasonic transducer according to embodiments of the present disclosure, and it is assumed that this method is implemented by utilizing the transducer assembly 10, which commonly includes an ultrasonic transducer 13 and an acoustic medium 15, and optionally further include a film 17 at an acoustic impedance boundary area when the acoustic medium 15 is water.

First, FIG. 4a shows an embodiment using total reflection inside the transducer assembly 10. Here, if no object comes into contact with an outer surface of the transducer assembly 10, the ultrasonic wave emitted from the ultrasonic transducer 13 is totally reflected in the transducer assembly 10 due to the difference in acoustic impedance between the acoustic medium 15 of the transducer assembly and the outer surface of the transducer assembly 10 (for example, the air), and the ultrasonic transducer 13 may receive the totally reflected response signal and measure a magnitude or energy amount thereof.

Second, FIG. 4b shows an embodiment for determining the degree of degradation of an ultrasonic transducer by using a signal reflected from a skin or a specific position of a phantom for measuring degradation. Here, it is possible to evaluate the degree of degradation by acquiring a pulse-echo signal before the surgical operation in a state where the theoretical transducer is in contact with an operation site of a patient and comparing it with a pulse-echo signal acquired at an early bio tissue. For this purpose, the transducer assembly 10 and the skin 420 need to come into contact through a separate acoustic medium 410 (for example, a coupling gel may be utilized).

More specifically, when a measurement target is brought into contact with the outer surface of the transducer assembly 10, an ultrasonic wave emitted from the ultrasonic transducer 10 sequentially passes through the acoustic medium 15 in the transducer assembly and the external separate acoustic medium 410 and is reflected at the measurement target, and the ultrasonic transducer 13 may receive the reflected response signal and measure a magnitude or energy amount thereof.

Third, FIG. 4c shows an embodiment using a steel reflector such as steel without using total reflection at the interface of the acoustic medium and the air. When the steel reflector 430 is brought into contact with the outer surface of the transducer assembly 10, an ultrasonic wave emitted from the ultrasonic transducer 13 passes through the acoustic medium 15 and is reflected by the steel reflector 430, and the ultrasonic transducer 13 may receive the reflected response signal and measure a magnitude or energy amount thereof.

Fourth, FIG. 4d does not use the total reflection at the interface of the acoustic medium and the air but uses a structural form of the cartridge to move the ultrasonic transducer 13 to an edge such that that a reflecting structure 19 such as a plastic housing case is utilized as a reflector, and such a reflection area 440 is depicted in FIG. 4d. By using this process, the degree of degradation may be evaluated by measuring a pulse-echo after moving the transducer to an end of the cartridge, rather than the film in the cartridge through which the ultrasonic wave may pass, and comparing it with a pulse-echo signal measured in the same environment.

More specifically, when the ultrasonic transducer 13 is relocated to face the reflecting structure 19 (for example the region 440) in the transducer assembly 10, an ultrasonic wave emitted from the ultrasonic transducer 13 passes through the acoustic medium 15 and is reflected by the reflecting structure 19 (for example, the region 440), and the ultrasonic transducer 13 may receive the reflected response signal and measure a magnitude or energy amount thereof.

FIG. 5 is a diagram for illustrating a method for determining a distance between an ultrasonic transducer and a film in a transducer assembly adopted by the ultrasonic system according embodiments of to the present disclosure, and the theoretical principle used in the drawings and abbreviations thereof are as follows.

$$T = \frac{1}{f}, \text{ where } f \text{ is frequency} \qquad \text{[Equation 1]}$$

$$\lambda = \frac{c}{f}, \qquad \text{[Equation 2]}$$

where $c$ is ultrasound speed (in water, 1480 m/s)

N: the number of cycles d: separated distance [Equation 3]

In other words, in FIG. 5(A), d represents a separation distance from the ultrasonic transducer 13 to the film 17.

Now, FIGS. 5(B) and 5(C) propose a theoretical basis on how to determine a separation distance d for solving the interference problem in the transmission and reception of ultrasonic waves.

First, in case of d≥2×N×λ, as shown in FIG. 5(B), after the ultrasonic wave is completely transmitted, the reflected ultrasonic signal is received, which does not cause interference. However, in case of d<2×N×λ, as shown in FIG. 5(C), while the ultrasonic wave is being continuously transmitted, the reflected ultrasonic signal is received, which causes interference 510.

In summary, the separation distance between the ultrasonic transducer 13 and the film 17 is proportional to the number of cycles of the ultrasonic signal emitted from the ultrasonic transducer 13 and is reversely proportional to the frequency of the ultrasonic signal. Thus, in order to transmit and receive the ultrasonic signal without interference, Equation 4 as below may be induced.

$$N \leq \frac{d}{2 \times \lambda} = \frac{d \times f}{2 \times c} \qquad \text{[Equation 4]}$$

Seeing Equation 4, a processing unit of the ultrasonic system according to an embodiment of the present disclosure may prevent interference between the signal emitted from the ultrasonic transducer 13 and the signal received thereto by setting the number of cycles of the ultrasonic signal emitted from the ultrasonic transducer 13 to be a half or less of a value obtained by multiplying the distance between the ultrasonic transducer 13 and the film 17 by a frequency of the ultrasonic signal and dividing by a speed of the ultrasonic signal.

FIG. 6 is a flowchart for illustrating a method for evaluating the performance of an ultrasonic transducer assembly which includes an ultrasonic transducer and an acoustic medium to transmit and receive an ultrasonic wave according to an embodiment of the present disclosure. Here, the features illustrated through FIG. 1 are described in a timewise manner and they are not described in detail here in order to avoid duplication of explanation.

In Step S610, a memory is used to store a reference signal value which represents the performance of the ultrasonic transducer.

In Step S620, the transducer assembly is controlled to emit an ultrasonic wave and a response (echo) signal is received to measure a magnitude or energy amount of the response signal. The response signal is generated as the ultrasonic wave emitted from the ultrasonic transducer is reflected or totally reflected due to the physical characteristics of the transducer assembly. This process of measuring a magnitude or energy amount of the response signal may be implemented by obtaining a reflected signal to a totally reflected signal in various manners described above with reference to FIGS. 4a to 4d.

In Step S630, the performance of the ultrasonic transducer is evaluated by comparing the value measured in Step S620 with the reference signal value stored in the memory by using an at least one processor.

FIG. 7 is a flowchart for illustrating a method for utilizing the method for evaluating performance of an ultrasonic transducer according to embodiments of the present disclosure to the ultrasonic system.

First, if an operating device is turned on, it is checked in Step S710 whether the therapeutic transducer connected to the system is a used cartridge. If the cartridge is not a used one, the process proceeds to Step S720 to perform the above-described pulse-echo test (the process of emitting an ultrasonic wave and receiving a response signal). After that, the energy amount or the magnitude of the incoming waveform is stored in the memory, and the treatment is performed through Step S750. The reference signal stored in Step S720 is used as a reference point for evaluating the degradation effect later after a predetermined time passes from the insertion of the transducer. If the inserted cartridge is not a new cartridge, the process proceeds to Step S730 to perform the pulse-echo test, and the energy and magnitude of the response signal are compared with the energy and magnitude of the reference signal stored previously in the same process (Step S720). At this time, if the measured energy compared to the reference energy is lowered below a certain value (a critical range may be set), a cartridge replacement is requested along with an alarm message. The critical range may be set using properties that to the degree of degradation of the ultrasonic transducer is proportional to the reduction of magnitude of the response signal. For example, if the amplitude of the received signal is not greater than the product of the amplitude of the reference signal and a threshold value as shown in Step S740, the process may proceed to Step S760 to display an alarm message to request the replacement of the cartridge. In a reverse case, it is determined that the therapeutic effect of the transducer is effective, and the treatment of Step S750 may be performed.

Meanwhile, since the ultrasonic wave propagates in water at a speed of 1480 m/s, the response signal takes a very short time of several microseconds to be received. Therefore, the ultrasonic wave may be used with ease whenever the equipment is booted or whenever a patient is changed, and the degree of degradation may be evaluated in a simple way. This procedure may be performed automatically by surgical equipment or manually by an operator.

According to the above mentioned present disclosure, based on the fact that a reflected signal is generated when an ultrasonic wave passes through a medium having different acoustic impedances, a signal is applied to an existing ultrasonic transducer, and a signal coming from the boundary between the acoustic medium and the air (for example, the acoustic medium may be water, and in this case, the boundary may be a film) is obtained, and the energy is quantitatively analyzed. In case of a periodically reflected signal, its magnitude is compared with the magnitude of the energy stored in the system through the same procedure as described above to determine whether the cartridge is normal or abnormal.

Meanwhile, in the embodiments of the present disclosure, the measurement may be performed in the following environments, in addition to the measurement method using the difference in acoustic impedance between water and air.

First, a phantom having a high reflection characteristic may be used in contact with a therapeutic transducer cartridge (a case filled with water) to enhance the transducer performance.

Second, a pulse-echo signal before the treatment may be obtained in a state where the therapeutic transducer is in contact with an operation site of a patient or a phantom for compensating for the deterioration, and then be compared with the pulse-echo signal acquired from the bio tissue at an early stage.

Third, the transducer may be moved to an end of the cartridge, rather than the film in the cartridge through which the ultrasonic wave may pass, and then the pulse-echo may be measured and compared with the pulse-echo signal measured in the same environment.

Meanwhile, the embodiments of the present disclosure may be implemented as computer-readable codes on a computer-readable recording medium. The computer-readable recording medium may include any kind of storage devices where data readable by a computer system is stored.

The computer-readable recording medium includes, for example, ROM, RAM, CD-ROM, a magnetic tape, a floppy disk, an optical data storage and the like. In addition, the computer-readable recording medium may be distributed to computer systems connected through a network so that computer-readable codes may be stored and executed in a distribution way. Also, functional programs, codes and code segments for implementing the present disclosure may be easily inferred by programmers in the related art.

Heretofore, various embodiments have been described. It will be understood by those skilled in the art that various modifications can be made without departing from the essential feature of the present disclosure. Thus, the disclosed embodiments should be considered as an illustrative purpose, rather than a restrictive purpose. The slope of the present disclosure is defined not in the above description but in the appended claims, and all equivalents within the same scope as the claims should be regarded as falling within the scope of the present disclosure.

INDUSTRIAL APPLICABILITY

The measurement method using a hydrophone, which is a conventional acoustic measurement technique, requires a system of a large magnitude and a complicated measuring method and also has a large restriction to an operator since it is too expensive. However, there has been no simple way to evaluate the degradation of the acoustic output, and thus it has been difficult to select an appropriate replacement time for a therapeutic ultrasonic transducer. Thus, a degraded ultrasonic transducer may be used for a surgical operation to deteriorate the therapeutic effect, and unnecessary expenditure may be caused due to the replacement of a normal cartridge.

In the embodiments of the present disclosure, by using the structure of the therapeutic ultrasonic transducer and the basic characteristics of the ultrasonic wave, it is possible to determine the degradation effect of the transducer in a short time, and it is possible to reduce time and cost since an operator needs not purchase a separate instrument or perform an environment in a specific environment. Moreover, since an appropriate replacement time may be selected for the therapeutic transducer, it is possible to keep the therapeutic effect of the ultrasonic treatment consistently and reduce the maintenance cost of the instrument by preventing unnecessary transducer replacement.

The invention claimed is:

1. An apparatus for evaluating performance of an ultrasonic transducer, comprising:
a transducer assembly comprising:
a body,
an ultrasonic transducer accommodated on a first end of the body and configured to generate an ultrasonic wave, receive a response signal, and measure a magnitude or energy amount of the response signal;
an acoustic medium filled in the body and configured to transmit the ultrasonic wave, and
an acoustic impedance boundary area formed at a second end of the body opposite the first end and in a direction in which the ultrasonic wave is emitted, and spaced apart from the ultrasonic transducer by a predetermined distance,
wherein the acoustic impedance boundary area comprises a material through which the ultrasonic wave transmits, and the body is a material that reflects the ultrasonic wave;
a storage unit comprising a memory configured to store a reference signal value which represents the performance of the ultrasonic transducer; and
a processing unit comprising a comparator configured to compare the measured value with the reference signal value stored in the storage unit to evaluate the performance of the ultrasonic transducer; and
wherein the ultrasonic transducer is moveable within the body to and from a position facing a reflecting structure formed in the body, the ultrasonic wave emitted from the ultrasonic transducer is reflected by the reflecting structure through the acoustic medium, and the ultrasonic transducer receives the reflected response signal to measure the magnitude or energy amount.

2. The apparatus for evaluating performance of an ultrasonic transducer according to claim 1,
wherein the response signal is generated when the ultrasonic wave emitted from the ultrasonic transducer is reflected or totally reflected according to a physical characteristic of the transducer assembly.

3. The apparatus for evaluating performance of an ultrasonic transducer according to claim 2,
wherein when no object comes into contact with an outer surface of the transducer assembly, the ultrasonic wave emitted from the ultrasonic transducer is totally reflected at an inside of the transducer assembly due to a difference in acoustic impedance between the acoustic medium of the transducer assembly and the outer surface of the transducer assembly, and the ultrasonic transducer receives the totally reflected response signal to measure the magnitude or energy amount.

4. The apparatus for evaluating performance of an ultrasonic transducer according to claim 2,
wherein when a measurement target comes into contact with an outer surface of the transducer assembly, the ultrasonic wave emitted from the ultrasonic transducer is reflected by the measurement target through the acoustic medium, and the ultrasonic transducer receives the reflected response signal to measure the magnitude or energy amount.

5. The apparatus for evaluating performance of an ultrasonic transducer according to claim 2,
wherein when a steel reflector comes into contact with an outer surface of the transducer assembly, the ultrasonic wave emitted from the ultrasonic transducer is reflected by the steel reflector through the acoustic medium, and the ultrasonic transducer receives the reflected response signal to measure the magnitude or energy amount.

6. The apparatus for evaluating performance of an ultrasonic transducer according to claim 1,
wherein the processing unit generates an alarm to notify that the performance of the ultrasonic transducer is degraded, when the difference between the reference signal value and the measured value is over a preset critical range.

7. The apparatus for evaluating performance of an ultrasonic transducer according to claim 6,
wherein the critical range is set using a property that the degree of degradation of the ultrasonic transducer is proportional to the degree of magnitude reduction of the response signal.

8. The apparatus for evaluating performance of an ultrasonic transducer according to claim 6,
wherein the transducer assembly is formed using an exchangeable cartridge and is controlled by the processing unit in a state of being inserted into a handpiece for ultrasonic treatment, and
wherein the alarm is a message which demands an exchange of the cartridge.

9. The apparatus for evaluating performance of an ultrasonic transducer according to claim 1,
wherein the distance between the ultrasonic transducer and the boundary area is proportional to the number of cycles of the ultrasonic signal emitted from the ultrasonic transducer and inversely proportional to a frequency of the ultrasonic signal.

10. The apparatus for evaluating performance of an ultrasonic transducer according to claim 1,
wherein the processing unit sets the number of cycles of the ultrasonic signal emitted from the ultrasonic transducer to be a half or less of a value obtained by multiplying the distance between the ultrasonic transducer and the boundary area by a frequency of the ultrasonic signal and dividing by a speed of the ultrasonic signal, thereby preventing an interference between the signal emitted from the ultrasonic transducer and the signal received thereto.

11. A method for evaluating performance of an ultrasonic transducer, which evaluates the performance of a transducer assembly having an ultrasonic transducer and an acoustic medium to transmit and receive an ultrasonic wave, the method comprising:
storing a reference signal value which represents the performance of the ultrasonic transducer by using a memory;
moving the ultrasonic transducer within a body configured to support the transducer assembly to a position where the ultrasonic transducer faces a reflecting structure formed in the body;
emitting an ultrasonic wave from the ultrasonic transducer through the acoustic medium toward the reflecting structure;
receiving a reflected response signal reflected by the reflecting structure;
measuring a magnitude or energy amount of the received response signal; and
comparing a measured value with the reference signal value stored in the memory by using at least one processor to evaluate the performance of the ultrasonic transducer.

12. The method for evaluating performance of an ultrasonic transducer according to claim 11,
wherein the response signal is generated when the ultrasonic wave emitted from the ultrasonic transducer is reflected or totally reflected according to a physical characteristic of the transducer assembly.

13. The method for evaluating performance of an ultrasonic transducer according to claim 12,
wherein the step of measuring a magnitude or energy amount of the response signal includes:
emitting an ultrasonic wave in a state where no object comes into contact with an outer surface of the transducer assembly;
receiving a totally reflected response signal by using the ultrasonic transducer as the ultrasonic wave emitted from the ultrasonic transducer is totally reflected at an inside of the transducer assembly due to a difference in acoustic impedance between the acoustic medium of the transducer assembly and the outer surface of the transducer assembly; and
measuring the magnitude or energy amount of the received response signal.

14. The method for evaluating performance of an ultrasonic transducer according to claim 12,
wherein the step of measuring a magnitude or energy amount of the response signal includes:
emitting an ultrasonic wave in a state where a measurement target comes into contact with an outer surface of the transducer assembly; receiving a reflected response signal by using the ultrasonic transducer as the ultrasonic wave emitted from the ultrasonic transducer is reflected by the measurement target through the acoustic medium; and
measuring a magnitude or energy amount of the received response signal.

15. The method for evaluating performance of an ultrasonic transducer according to claim 12,
wherein the step of measuring a magnitude or energy amount of the response signal includes:
emitting an ultrasonic wave in a state where a steel reflector comes into contact with an outer surface of the transducer assembly;
receiving a reflected response signal by using the ultrasonic transducer as the ultrasonic wave emitted from the ultrasonic transducer is reflected by the steel reflector through the acoustic medium; and
measuring a magnitude or energy amount of the received response signal.

16. The method for evaluating performance of an ultrasonic transducer according to claim 11, further comprising:
generating an alarm to notify that the performance of the ultrasonic transducer is degraded, when a difference between the reference signal value and the measured value is over a preset critical range.

17. The method for evaluating performance of an ultrasonic transducer according to claim 16, wherein the critical range is set using a property that the degree of degradation of the ultrasonic transducer is proportional to the degree of magnitude reduction of the response signal.

18. The method for evaluating performance of an ultrasonic transducer according to claim 16, wherein the transducer assembly includes a body configured to support the transducer assembly, an ultrasonic transducer accommodated in the body and configured to generate an ultrasonic wave, a boundary area spaced apart from the ultrasonic transducer by a predetermined distance and formed at an end of the body in a direction in which the ultrasonic wave is emitted, and the acoustic medium filled in the body to transmit the ultrasonic wave, and wherein the number of cycles of the ultrasonic signal emitted from the ultrasonic transducer is set to be a half or less of a value obtained by multiplying the distance between the ultrasonic transducer and the boundary area by a frequency of the ultrasonic signal and dividing by a speed of the ultrasonic signal, thereby preventing an interference between the signal emitted from the ultrasonic transducer and the signal received thereto.

19. A non-transitory computer-readable recording medium in which a program for executing the method of claim 11 in a computer is recorded.

* * * * *